United States Patent
Valentin

(10) Patent No.: US 12,214,178 B2
(45) Date of Patent: Feb. 4, 2025

(54) TOOL FOR REMOVING A CAP FROM A MEDICAL INJECTION DEVICE

(71) Applicant: Becton Dickinson France, Le Pont de Claix (FR)

(72) Inventor: Stéphane Valentin, L'Albenc (FR)

(73) Assignee: Becton Dickinson France, Le Pont de Claix (FR)

( * ) Notice: Subject to any disclaimer, the term of this patent is extended or adjusted under 35 U.S.C. 154(b) by 581 days.

(21) Appl. No.: 17/046,403

(22) PCT Filed: Apr. 9, 2019

(86) PCT No.: PCT/EP2019/058910
§ 371 (c)(1),
(2) Date: Oct. 9, 2020

(87) PCT Pub. No.: WO2019/197381
PCT Pub. Date: Oct. 17, 2019

(65) Prior Publication Data
US 2021/0030972 A1    Feb. 4, 2021

(30) Foreign Application Priority Data

Apr. 11, 2018    (EP) .................................... 18305434

(51) Int. Cl.
*A61M 5/32*    (2006.01)
(52) U.S. Cl.
CPC ... *A61M 5/3204* (2013.01); *A61M 2205/0216* (2013.01)

(58) Field of Classification Search
CPC ........ A61M 5/3204; A61M 2205/0216; A61M 2205/192; A61M 2005/3104; A61M 5/3219; B25B 9/04
See application file for complete search history.

(56) References Cited

U.S. PATENT DOCUMENTS

| | | | |
|---|---|---|---|
| 9,233,212 B2 * | 1/2016 | Holmqvist | A61M 5/3204 |
| 10,166,342 B2 * | 1/2019 | Protasiewicz | A61M 5/3202 |
| 10,335,553 B2 | 7/2019 | Bendek | |
| 10,661,024 B2 * | 5/2020 | Allen | A61M 5/3204 |

(Continued)

FOREIGN PATENT DOCUMENTS

| | | |
|---|---|---|
| EP | 3047868 A1 | 7/2016 |
| EP | 3222313 A1 | 9/2017 |

(Continued)

*Primary Examiner* — Nathan R Price
*Assistant Examiner* — Fatimata Sahra Diop
(74) *Attorney, Agent, or Firm* — The Webb Law Firm

(57) ABSTRACT

A tool for removing a cap from a medical injection device comprising a body and a needle extending distally from the body, the cap covering the needle, the tool being characterized in that it comprises a pair of opposite jaws connected by an elastic interface, each jaw comprising: a distal portion forming a distal clamp configured to surround at least a part of the cap; and a proximal portion forming a proximal clamp configured to be removably axially fixed to a body of the medical injection device, the elastic interface forming a fulcrum located between the distal and proximal portions such that a pinching force exerted radially inwardly onto the distal portion of the jaws causes the proximal portion of the jaws to expand radially outwardly.

19 Claims, 3 Drawing Sheets

(56) References Cited

U.S. PATENT DOCUMENTS

| | | | |
|---|---|---|---|
| 10,814,070 B2 | 10/2020 | Riedel et al. | |
| 11,311,681 B2* | 4/2022 | Groetzbach | A61M 5/3202 |
| 2016/0325051 A1* | 11/2016 | Keim | A61M 5/20 |
| 2017/0274151 A1 | 9/2017 | Allen | |
| 2020/0306460 A1* | 10/2020 | Ando | A61M 5/3204 |
| 2021/0220619 A1* | 7/2021 | Farrell | A61M 5/326 |

FOREIGN PATENT DOCUMENTS

| | | |
|---|---|---|
| EP | 3257540 A1 | 12/2017 |
| JP | 2016526996 A | 9/2006 |
| WO | 2015007857 A1 | 1/2015 |
| WO | 2017089266 A1 | 6/2017 |
| WO | 2018011417 A1 | 1/2018 |

* cited by examiner

TOOL FOR REMOVING A CAP FROM A MEDICAL INJECTION DEVICE

CROSS-REFERENCE TO RELATED APPLICATIONS

This application is the United States national phase of International Application No. PCT/EP2019/058910 filed Apr. 9, 2019, and claims priority to European Patent Application No. 18305434.5 filed Apr. 11, 2018, the disclosures of which are hereby incorporated by reference in their entirety.

FIELD OF THE INVENTION

The invention relates to a tool for removing a cap from a medical injection device.

BACKGROUND OF THE INVENTION

A medical injection device comprising a needle is generally closed by a cap that protects the needle from external shocks and/or contamination, ensures a fluid-tight closure for the content of the medical injection device, and also protects a user from needle stick injuries. Depending on the application, the cap may be a needle shield made of a soft material, such as rubber, TPE (thermoplastic elastomer) or another elastomer, a rigid shield made of a substantially rigid material, such as plastic, or a rigid needle shield comprising a needle shield arranged in a rigid shield.

When the cap is placed on the medical injection device, the needle tip penetrates a distal portion of the needle shield if any, or is at a distance of the inner surface of the rigid shield, in the absence of any needle shield. Besides, the proximal portion of the cap is in contact with the distal end of the barrel of the medical container.

The cap is designed so as to require a certain pull-out force to be removed. Said pull-out force has to be sufficiently high so as to avoid any accidental removal of the cap. However, if the pull-out force is too high, the medical injection device is not convenient for use by a patient or medical staff. Indeed, since the outer surface of the cap is substantially smooth and/or since the cap is substantially small, the user may not grip it properly.

In particular, when the medical injection device is provided with a safety device, which is intended to protect the needle tip after the injection, the safety device itself may hinder access to the cap.

Cap removers have been proposed to assist the removal of the cap.

However, such cap removers may not be fully satisfactory. In particular, the cap remover is usually brought into contact with the cap by an axial movement of the cap remover in the proximal direction. During this movement, the cap remover may exert an effort onto the cap in the proximal direction. Depending on its intensity, such an effort may cause the medical injection device to be withdrawn from the safety device, cause the needle to pierce the soft material if any and bring back small residues of the soft material (said effect is called coring), and/or deform the needle. This may also result in a loss of tightness between the cap and the medical injection device.

SUMMARY OF THE INVENTION

A goal of the invention is to provide a tool for removing a cap that is easy to use and that prevents any coring of the inner shield (if any) during manipulation of said tool.

To that end, an object of the invention is a tool for removing a cap from a medical injection device comprising a body and a needle extending distally from the body, the cap covering the needle, said tool being characterized in that it comprises a pair of opposite jaws connected by an elastic interface, each jaw comprising:
- a distal portion forming a distal clamp configured to surround at least a part of the cap; and
- a proximal portion forming a proximal clamp configured to be removably axially fixed to a body of the medical injection device;
- the elastic interface forming a fulcrum located between the distal and proximal portions such that a pinching force exerted radially inwardly onto the distal portion of the jaws causes the proximal portion of the jaws to expand radially outwardly;
- the tool being operable between:
- a rest position wherein the proximal portion of the jaws rigidly engages the body of the medical injection device, the distal portion of the jaws being distant from the cap, and
- an operative position wherein the distal portion of the jaws is pinched so that said distal portion engages the cap and the proximal portion disengages from the body of the medical injection device.

In the present text, the terms "tool for removing a cap", "cap removal tool" and "removal tool" designate the same object.

In the present text, the cap may be a needle shield made of a soft material, such as rubber or another elastomer, a rigid shield made of a substantially rigid material, such as plastic, or a rigid needle shield (usually designated by acronym RNS) which comprises a needle shield arranged in a rigid shield.

In the present text, the distal end of the medical injection device should be understood as meaning the end farthest from the hand of the user handling the medical injection device and the proximal end must be understood as meaning the end closest to the hand of said user. As such, the distal direction should be understood as the direction farther away from the hand of the user, and the proximal direction is the opposite direction, i.e., the direction towards the hand of the user. The proximal and distal directions are parallel to the needle. The radial direction should be understood as the direction perpendicular to the proximal and distal directions. As far as the cap removal tool is concerned, the terms "distal" and "proximal" are also used with reference to the medical injection device and not with reference to the hand of the user manipulating the removal tool. In other words, a distal end of the cap removal tool is farthest from the medical injection device than a proximal end of the cap removal tool, although the user may handle said distal part to use the cap removal tool.

Such a cap removal tool has the advantage of not exerting any axial effort onto the cap in the proximal direction, either when the cap removal tool is connected to the medical injection device or when the cap removal tool is operated to remove the cap from the medical injection device.

According to an embodiment, the distal portion of each jaw comprises a gripping section extending on an inner surface thereof. Such a gripping section ensures a sufficient engagement of the distal clamp with the cap so as to facilitate the removal of the cap when the cap removal tool is pulled in the distal direction.

According to an embodiment, said gripping section comprises at least one pad made of a soft material configured to generate a frictional engagement with the cap when the tool is in the operative position. Said soft material may be selected from: rubber, SBS (styrene-butadiene-styrene block copolymer), SEBS (styrene-ethylene-butadiene-styrene block copolymer) and polyurethane.

Alternatively, the gripping section of each jaw comprises at least one blade configured to grip into the cap when the tool is in the operative position. Said blade may be made of stainless steel.

According to an embodiment, the distal portion of each jaw comprises a gripping zone extending on an outer surface thereof. Said gripping zone is configured to provide a better handling of the cap removal tool by the user, especially when pulling the cap removal tool in the distal direction.

According to an embodiment, the distal portion of each jaw comprises a locking mechanism configured to lock the distal clamp in the operative position. Thanks to such a locking mechanism, the user only has to exert a pulling force onto the distal clamp in the distal direction to remove the cap. Said locking mechanism may be formed of interlocking elements facing each other on said distal portions of the jaws.

According to an embodiment, the proximal portion of each jaw is configured to provide a snap-in engagement with the body of the medical injection device in the rest position.

According to an embodiment, the jaws comprise a rigid polymeric material, such as ABS (acrylonitrile butadiene styrene), PC (polycarbonate), PC/ABS (polycarbonate/acrylonitrile butadiene styrene) or POM (polyoxymethylene).

Another object of the invention is a medical injection assembly comprising a medical injection device including a body, a needle extending distally from the body and a cap covering the needle, and a cap removal tool as described above, wherein the proximal portion of the jaws rigidly engages the body of the medical injection device and the distal portion of the jaws is distant from the cap.

According to an embodiment, the medical injection device comprises a safety device and the proximal portions of the jaws engage a part of said safety device.

According to another embodiment, the medical injection device comprises a syringe and the proximal portion of the jaws engages a part of said syringe.

Another object of the invention is a method for removing a cap from a medical injection device. Said method, comprises the following successive steps:
  providing a cap removal tool as described above;
  engaging the proximal portion of the jaws onto a body of the medical injection device without contacting the cap, the tool being in the rest position;
  pinching the distal portion of the jaws so as to engage the cap, the tool being in the operative position; and
  pulling the distal portion of the jaws in the distal direction to remove the cap from the medical injection device.

BRIEF DESCRIPTION OF THE FIGURES

Further features, effects and advantages of the invention will appear in the detailed description to follow, based on the appended drawings, wherein.

DETAILED DESCRIPTION OF EMBODIMENTS OF THE INVENTION

Figure 1:
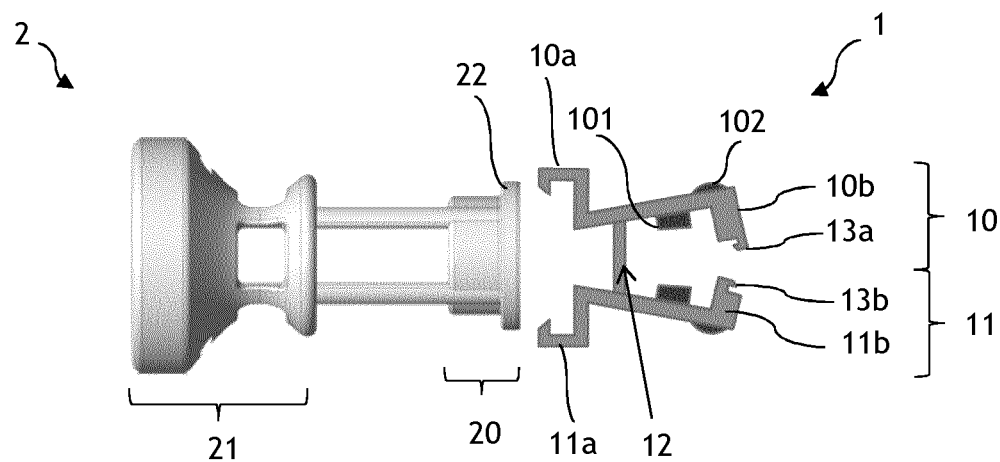
FIG. 1 illustrates a cap removal tool according to an embodiment of the invention, before its assembly to a safety device.

The cap removal tool comprises a pair of opposite jaws that are connected by an elastic interface about which they are pivotable.

Each jaw comprises a distal portion configured to surround at least a part of the cap, and a proximal portion configured to cooperate with a part of the medical injection device distinct from the cap. More precisely, the medical injection device preferably comprises a body from which a needle extends distally. The body may be a barrel of a syringe, a housing of a safety device surrounding the barrel of the syringe, a housing of an injector configured to receive the barrel of a syringe, an ergonomic shell, etc.

The proximal portions of the jaws preferably comprise connection means configured to axially attach the removal tool to the body of the medical injection device. The connection means are configured to axially fix the removal tool to the body. The connection means may comprise one or several of the followings elements: snap features, one or several hook(s), one or several protrusions. Such an attachment is reversible, meaning that the removal tool can be detached from the body of the medical injection device.

The distal portions of the jaws preferably comprise a gripping section configured to grip the cap.

The elastic interface that connects the jaws forms a fulcrum located between the distal and proximal portions, such that a pinching force exerted radially inwardly onto the distal portion of the jaws causes the proximal portion of the jaws to expand radially outwardly. Conversely, a pinching force exerted radially inwardly onto the proximal portion of the jaws causes the distal portion of the jaws to expand radially outwardly. In other words, the proximal portions of the jaws together form a proximal clamp, whereas the distal portions of the jaws together form a distal clamp, said clamps operating in opposition to each other. When the proximal clamp is closed, the distal clamp is open and conversely, when the proximal clamp is open, the distal clamp is closed.

Thanks to this structure, the cap removal tool is operable between the following positions:
  a rest position wherein the proximal portion of the jaws is axially fixed to a part of the medical injection device (the proximal clamp being closed), the distal portion of the jaws being distant from the cap (the distal clamp being open), and
  an operative position wherein the distal portion of the jaws is pinched so that said distal portion engages the cap (the distal clamp being closed) and the proximal portion of the jaws disengages from the medical injection device (the proximal clamp being open).

In rest position, the proximal clamp is closed and the connection means engage the body so that the removal tool is axially fixed relative to the body, while the distal clamp is open and the removal tool does not contact the cap. In operative position, the proximal clamp is open, the connection means do not engage the body of the medical injection device, while the distal clamp is closed so that the gripping section engages the cap so that when the removal tool is axially pulled, the cap is axially pulled together with the removal tool.

In rest position, the connection between the proximal clamp and the body of the medical injection device provides an axial abutment for the cap removal tool relative to the body of the medical injection device in the proximal direction. Said connection may be provided by any suitable means providing an axial fixation of the cap removal tool to the medical injection device, such as a hook, a snap-in connection, a bayonet, etc.

In operative position, the distal clamp is configured to pinch the cap so that when the removal tool is pulled from the medical injection device the cap is pulled with the removal tool. According to an embodiment, the rest position is the position of the cap removal tool when the medical injection device is being stored, until a user prepares for an injection. The cap removal tool is then moved to the operative position to remove the cap from the medical injection device so as to expose the needle tip in order to carry out the injection.

The cap removal tool may be used with any medical injection device. In some embodiments, the medical injection device may be a syringe alone. In other embodiments, the medical injection device may be a syringe equipped with any type of safety device or with any shell surrounding at least part of the syringe. For example, the shell could be an ergonomic shell configured to ease the manipulation of a syringe. The medical injection device could also be an auto-injector or a manual injector.

FIG. 1-6 illustrate an embodiment of the cap removal tool according to the invention, designed to cooperate with an ergonomic shell intended to be clipped onto a medical container.

With reference to FIG. 1, the cap removal tool 1 is first provided separately from the ergonomic shell 2. The shell 2 comprises a proximal portion 21 adapted to be coupled to the proximal end of a syringe (see FIG. 4) and a distal portion 20 comprising a radial flange 22.

The cap removal tool 1 comprises a pair of opposite jaws 10, 11. Each jaw 10, 11 comprises a respective distal portion 10b, 11b and a respective proximal portion 10a, 11a that is intended to be coupled to a distal end of the shell 2. The junction between the distal and proximal portion of each jaw is rigid, meaning that it does not deform during operation of the tool. The interface 12 that connects the jaws between the distal and proximal portions is elastic and forms a fulcrum about which the jaws are pivotable.

The distal portions 10b, 11b of the jaws together form a distal clamp that can be operated between an open and a closed position. Similarly, the proximal portions 10a, 11a of the jaws together form a proximal clamp that can be operated between an open and a closed position opposite to the position of the distal clamp.

The proximal portion 10a, 11a is advantageously configured to provide a snap-in engagement with the shell 2, or more generally with the body of the medical injection device. To that end, the proximal ends 10a, 11a present a hook shape, which provides a mechanical connection with the flange 22. The hook shape preferably substantially corresponds to the shape of the radial flange 22. However, in other embodiments, the shell may not comprise such a flange. For example, the body of the medical injection device may comprise grooves or holes formed in its outer surface, and the proximal portions 10a, 11a may be configured to engage said grooves or holes. In case the body of the medical injection device does not comprise any specific snap-in feature, the proximal portions of the jaws may simply be configured to be applied onto the outer surface of the body.

In the initial position shown in FIG. 1, both distal and proximal clamps are half-way open.

Figure 2:
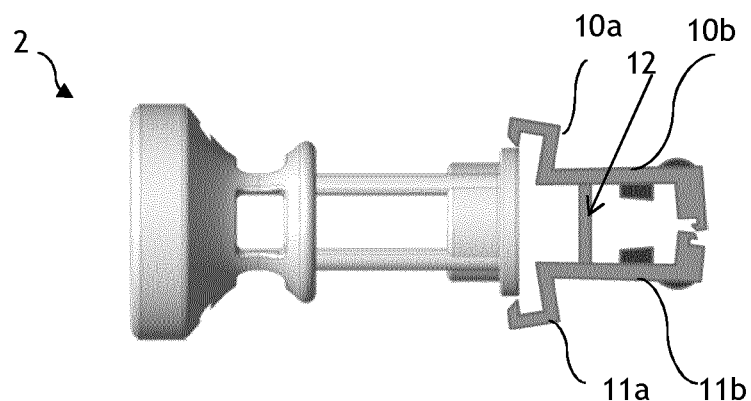
FIG. 2 illustrates the cap removal tool of FIG. 1 during its assembly to the safety device.

Referring to FIG. 2, to assemble the cap removal tool 1 to the shell 2, the cap removal tool 1 is pushed onto the distal end of the shell. Under this pushing force, the clamp formed by the proximal portions 10a, 11a opens until the hooks pass over the flange 22 whereas the clamp formed by the distal portions 10b, 11b closes. Then, once the hooks extend over the periphery of the flange 22 (see FIG. 3), the clamp formed by the distal portions 10b, 11b opens again.

Figure 3:
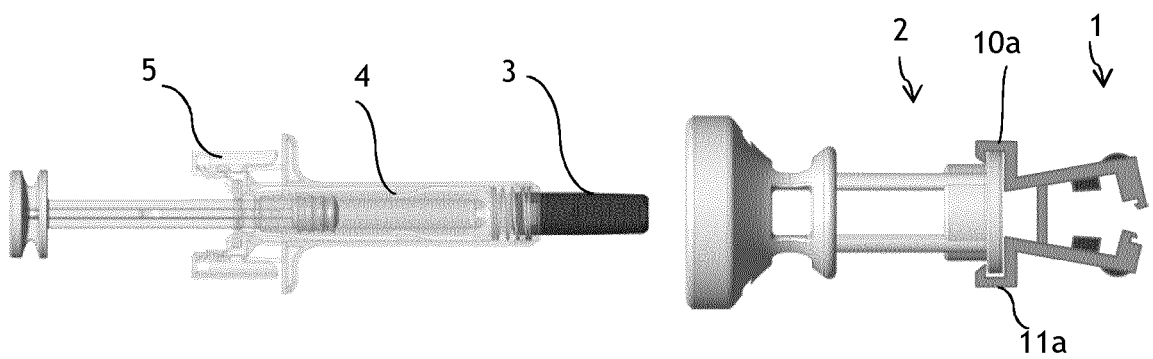
FIG. 3 illustrates the assembly of FIG. 2 before its coupling to a medical injection device provided with a cap.

FIG. 3 represents the rest position of the cap removal tool 1. In this position, the removal tool is axially fixed to the shell. The distal portions 10b, 11b of the jaws are spaced one from each other, such that a cap may inserted into the removal tool without radially contacting the distal portions 10b, 11b of the jaws.

After the removal tool 1 has been coupled to the shell, an assembly comprising a syringe 4 comprising a needle (not shown) and a cap 3 protecting the needle, and a safety device 5 coupled to the syringe, is inserted into the shell. Advantageously, the safety device 5 is clipped into the shell 2. The assembly comprising the syringe, the cap and the safety device may be inserted in the set comprising the shell and the removal tool since the removal tool is configured to not contact the cap as long as it is fixed to the shell.

Figure 4:
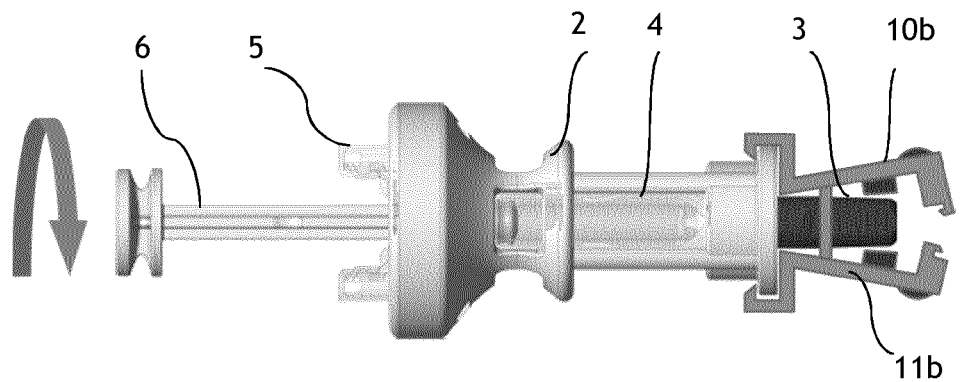
FIG. 4 illustrates the medical injection device of FIG. 3 with the assembly coupled thereto.

Referring to FIG. 4, once the assembly comprising the safety device 5 and the syringe has been assembled to the shell 2, the distal portion 10b, 11b of the jaws 10, 11 extends around the cap 3, without contacting it. The internal dimensions of the removal tool 1 are chosen so as to avoid any contact with the cap 3 when the removal tool 1 is in the rest position. In particular, even in case of a spin movement of the assembly comprising the safety device and the syringe is imparted by the plunger 6 (indicated by the arrow), no effort is exerted by the removal tool 1 onto the cap.

It is to be noted that also in the assembling step of FIG. 3 the removal tool 1 does not enter into contact with the cap 3. In particular, the hook formed by the proximal portion of the jaws provides an axial abutment for the removal tool 1 in the proximal direction, thereby avoiding any axial movement of the cap caused by the removal tool 1.

Thus, the risk of deformation of the needle, coring of the needle shield (if any) and resulting loss of tightness is thereby prevented.

Advantageously, the cap may be visualized thorough an opening arranged between the jaws.

Figure 5:
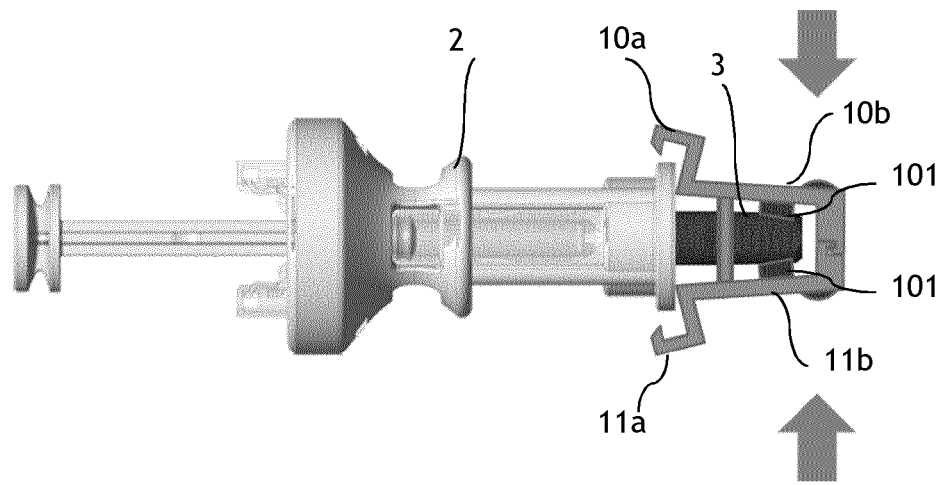
FIG. 5 illustrates the application of a pinching force onto the distal portion of the cap removal tool of FIG. 4.

Referring to FIG. 5, when the user intends to carry out an injection, he/she pinches the distal portion 10b, 11b of the jaws to bring them closer to each other in the radial direction (indicated by the arrows), whereas the proximal portions 10a, 11a are brought apart from each other.

The cap removal tool 1 is then in the operative position.

According to an advantageous embodiment, the distal portion comprises a locking mechanism configured to lock the distal portions 10b, 11b in the operative position.

For example, said locking mechanism may be formed of interlocking elements 13a, 13b facing each other on said members 10b, 11b, with complementary shapes. However, any other locking feature may be used. The interlocking elements may be placed at an end of the jaws as represented on FIG. 1, and/or they may be placed on both sides of the jaws.

The locking may be reversible (i.e. allowing unlocking the distal portion) or not.

When the removal tool 1 is in the operative position, the distal portions 10*b*, 11*b* engage the cap 3. It is to be noted that this engagement does not imply any relative axial movement of the removal tool 1, but only a radial pressure exerted by the distal portions 10*b*, 11*b*. The risk of deformation of the needle, coring of the inner shield (if any) and resulting loss of tightness is thereby prevented.

Preferably, the distal portions 10*b*, 11*b* comprise a gripping section 101 extending on an inner surface thereof.

According to an embodiment, said gripping section comprises at least one pad made of a soft material configured to generate a frictional engagement with the cap when the tool is in the operative position, the pad being urged by the portion 10*b*, 11*b* onto the cap. For example, said soft material may be selected from: rubber, SBS (styrene-butadiene-styrene block copolymer), SEBS (styrene-ethylene-butadiene-styrene block copolymer) and polyurethane. The pad is designed so as to have a sufficiently large contact surface with the cap.

According to an alternative embodiment, the gripping section comprises at least one rigid blade configured to grip into the cap when the removal tool is in the operative position. For example, said blade may be made of stainless steel. The blade may have a single continuous sharp edge or a plurality of teeth. The blade is preferably arranged radially in a plane perpendicular to the distal direction, in order to avoid any relative sliding of the blade and the cap.

In said operative position, the proximal clamp opens sufficiently to free the flange 22 of the shell 2.

Figure 6:
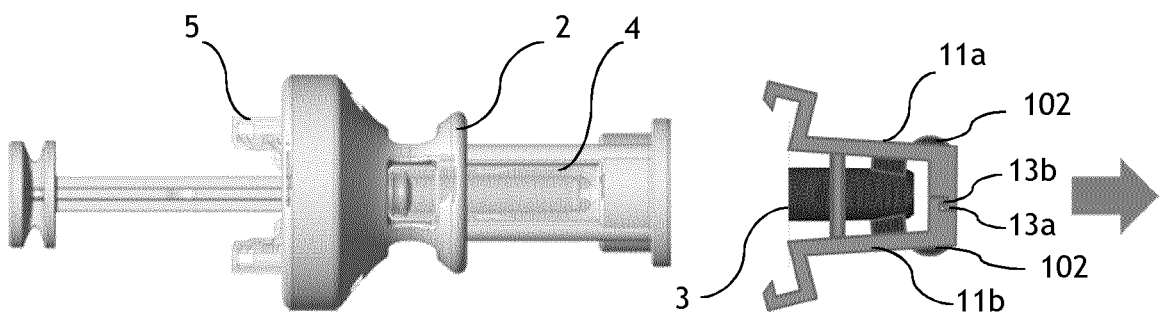
FIG. 6 illustrates the removal of the cap from the medical injection device of FIG. 5.

Thus, referring to FIG. 6, the user may withdraw the cap 3 from the medical injection device by pulling the removal tool 1 in the distal direction (represented by the arrow). The cap 3 is still maintained in the removal tool 1 by the radial pressure exerted by the distal clamp.

Advantageously, the distal portions 10*b*, 11*b* of the jaws comprises a gripping zone 102 extending on an outer surface thereof, possibly forming a slight protrusion. Said gripping zone may be made of a soft material, such as rubber, SBS, SEBS or polyurethane. The gripping zone provides a better grip for the user's fingers when removing the cap.

Thanks to the ergonomics of the distal clamp, the removal tool 1 is a convenient tool to remove the cap, since it offers to the user an easier access and a better grip than the cap itself.

Besides, with the locking mechanism of the distal clamp, once the removal tool is in operative position, the user only has to perform a simple axial movement in the distal direction.

In the absence of such a locking mechanism, the user has to perform a combined pinching movement, to grip the cap, and axial movement, to pull the cap out of the medical injection device.

In addition, the locking mechanism of the distal clamp also has the advantage of maintaining the cap in the removal tool after its withdrawal from the medical injection device.

The jaws 10, 11 may be made of polymeric materials, such as ABS (acrylonitrile butadiene styrene), PC (polycarbonate), PC/ABS (polycarbonate/acrylonitrile butadiene styrene) or POM (polyoxymethylene). The interface 12 is preferably in the same material as the jaws, with a shape and thickness adapted to provide the required elasticity. The jaws and the interface may thus be made of a single piece, e.g. made by injection molding.

When applicable, the gripping section and/or the gripping zone may be integral with the distal portions, e.g. by bi-component injection or overmolding. Otherwise, the gripping section and/or the gripping zone may be fixed to the distal portions, e.g. by bonding or welding, after the distal portion of each jaw is formed.

Figure 7:
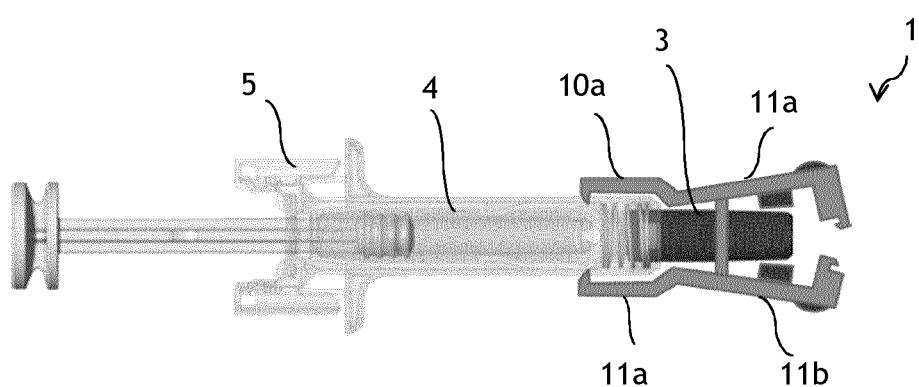
FIG. 7 illustrates a cap removal tool according to another embodiment of the invention.

FIG. 7 illustrates another embodiment of the removal tool according to the invention, adapted to cooperate with the safety device itself, the syringe being clipped into the safety device. The reference signs that are already present in FIGS. 1-6 represent the same components.

The design of the removal tool 1 is slightly different to accommodate the design of the safety device 5. However, it is operated in the same way as described above.

Of course, the device may be used with other types of medical injection devices or safety devices. The skilled person is able to design the proximal part of the cap removal tool to be able to engage the syringe, shell or safety device.

Advantageously, the product provided to the user comprises the syringe, the safety device (if any), the shell (if any) (all forming the medical injection device), the cap and the cap removal tool already assembled together, in a protective packaging.

According to an embodiment, the cap removal tool is in the rest position (as shown in FIG. 4). The user thus has to pinch the distal portions to close the distal clamp and then pull the cap out of the medical injection device.

Alternatively, the cap removal tool may be locked in the operative position (as shown in FIG. 5) during the assembly at the manufacturing plant. Thus, the user only has to exert a pulling force in the distal direction to remove the cap. Even if the cap removal tool is in contact with the cap before being delivered to the user, since the assembly is in a protective packaging, the cap is not subjected to any axial effort, and the risk of damaging the cap or losing integrity or tightness is low.

Although not illustrated, the cap removal tool can also be connected directly to the syringe.

The invention claimed is:

1. A tool for removing a cap from a medical injection device comprising:
   a body and a needle extending distally from the body, the cap covering the needle, wherein the tool comprises a pair of oppositely positioned jaws connected by an elastic interface, each jaw comprising:
      a distal portion forming a distal clamp configured to surround at least a part of the cap; and
      a proximal portion forming a U-shaped proximal hook portion on the proximal end of each of the pair of jaws, the U-shaped proximal hook portions configured to be removably axially fixed to a body of the medical injection device, wherein the U-shaped proximal hook portions of the jaws are oriented such that each U-shaped opening in the U-shaped proximal hook portions face radially inward,
   wherein the elastic interface forming a fulcrum located between the distal portion and the U-shaped proximal hook portions such that a pinching force exerted radially inwardly onto the distal portion of the jaws causes the U-shaped proximal hook portions of the jaws to expand radially outwardly, and
   wherein the tool is operable between:
   a rest position wherein the U-shaped proximal hook portions of the jaws rigidly engages the body of the medical injection device, the distal portion of the jaws being distant from the cap; and
   an operative position wherein the distal portion of the jaws is pinched so that the distal portion engages the cap and the U-shaped proximal hook portions disengage from the body of the medical injection device.

2. The tool of claim 1, wherein the distal portion of each jaw comprises a gripping section extending on an inner surface thereof.

3. The tool of claim 2, wherein the gripping section comprises at least one pad made of a soft material configured to generate a frictional engagement with the cap when the tool is in the operative position.

4. The tool of claim 3, wherein the soft material is selected from a group of rubber, SBS (styrene-butadiene-styrene block copolymer), SEBS (styrene-ethylene-butadiene-styrene block copolymer) and polyurethane.

5. The tool of claim 2, wherein the gripping section of each jaw comprises at least one blade configured to grip into the cap when the tool is in the operative position.

6. The tool of claim 5, wherein the blade is made of stainless steel.

7. The tool of claim 1, wherein the distal portion of each jaw comprises a gripping zone extending on an outer surface thereof.

8. The tool of claim 1, wherein the distal portion of each jaw comprises a locking mechanism configured to lock the distal clamp in the operative position.

9. The tool of claim 8, wherein the locking mechanism is formed of interlocking elements facing each other on the distal portions.

10. The tool of claim 1, wherein the proximal portion of each jaw is configured to provide a snap-in engagement with the body of the medical injection device in the rest position.

11. The tool of claim 1, wherein the jaws comprise a rigid polymeric material, such as ABS (acrylonitrile butadiene styrene), PC (polycarbonate), PC/ABS (polycarbonate/acrylonitrile butadiene styrene) or POM (polyoxymethylene).

12. A medical injection assembly comprising:
   a medical injection device including a body, a needle extending distally form the body and a cap covering the needle; and
   a tool as claimed in claim 1,
   wherein the U-shaped proximal hook portions of the jaws rigidly engage the body of the medical injection device and the distal portion of the jaws is distant from the cap.

13. The medical injection assembly of claim 12, wherein the medical injection device comprises a safety device and the U-shaped proximal hook portions of the jaws engage a part of the safety device.

14. The medical injection assembly according to claim 13, wherein the medical injection device comprises a syringe and the U-shaped proximal hook portions of the jaws engages a part of the syringe.

15. A method for removing a cap from a medical injection device, comprising the following successive steps:
   providing a tool according to claim 1;
   engaging the U-shaped proximal hook portions of the jaws onto a body of the medical injection device without contacting the cap, the tool being in the rest position;
   pinching the distal portion of the jaws so as to engage the cap, the tool being in the operative position; and
   pulling the distal portion of the jaws in the distal direction to remove the cap from the medical injection device.

16. The tool of claim 1, wherein the distal portion of each jaw comprises an L-shaped gripping section extending on an inner surface thereof.

17. The medical injection assembly of claim 12, wherein the distal portion of each jaw comprises an L-shaped gripping section extending on an inner surface thereof.

18. The tool of claim 16, wherein each L-shaped gripping section further comprises a locking mechanism configured to lock each L-shaped gripping portion to one another in the operative position.

19. The medical injection assembly of claim 17, wherein each L-shaped gripping section further comprises a locking mechanism configured to lock each L-shaped gripping portion to one another in the operative position.

* * * * *